(12) United States Patent
Schuman

(10) Patent No.: US 10,314,664 B2
(45) Date of Patent: Jun. 11, 2019

(54) TISSUE-REMOVING CATHETER AND TISSUE-REMOVING ELEMENT WITH DEPTH STOP

(71) Applicant: Covidien LP, Mansfield, MA (US)

(72) Inventor: Victoria Schuman, Minneapolis, MN (US)

(73) Assignee: Covidien LP, Mansfield, MA (US)

( * ) Notice: Subject to any disclaimer, the term of this patent is extended or adjusted under 35 U.S.C. 154(b) by 186 days.

(21) Appl. No.: 14/877,097

(22) Filed: Oct. 7, 2015

(65) Prior Publication Data

US 2017/0100150 A1 Apr. 13, 2017

(51) Int. Cl.
*A61B 90/00* (2016.01)
*A61B 17/3207* (2006.01)

(52) U.S. Cl.
CPC ...... *A61B 90/03* (2016.02); *A61B 17/320783* (2013.01); *A61B 17/320758* (2013.01); *A61B 2017/320791* (2013.01); *A61B 2090/033* (2016.02); *A61B 2090/034* (2016.02)

(58) Field of Classification Search
CPC . A61B 17/3205; A61B 17/3207; A61B 90/03; A61B 2017/320716; A61B 2017/320725; A61B 2017/320733; A61B 2017/320741; A61B 2017/320758; A61B 2017/32075; A61B 2017/320766; A61B 2017/320775; A61B 2017/320791; A61B 17/320783
See application file for complete search history.

(56) References Cited

U.S. PATENT DOCUMENTS

| 1,481,078 A | 1/1924 | Albertson |
| 2,178,790 A | 11/1939 | Henry |
| 2,701,559 A | 2/1955 | Cooper |

(Continued)

FOREIGN PATENT DOCUMENTS

| CA | 2000621 | 4/1990 |
| DE | 3732236 C1 | 12/1988 |

(Continued)

OTHER PUBLICATIONS

Amplatz Coronary Catheters, posted: Feb. 25, 2009, [online], [retrieved on Mar. 29, 2011], retrieved from the Cardiophile MD using Internet website <URL:http://cardiophile.org/2009/02/amplatzcoronary-catheter.html> (3 pages).

(Continued)

*Primary Examiner* — Todd J Scherbel
*Assistant Examiner* — Brooke Labranche

(57) ABSTRACT

A tissue-removing catheter includes a tissue-removing element operably connected to a drive shaft for rotation of the tissue-removing element about an axis of rotation in a cutting direction. The tissue-removing element includes a cutting edge that extends around the axis of rotation and a depth stop that extends around the axis of rotation radially inward of the cutting edge relative to the axis of rotation. The depth stop defines an engagement surface adapted to engage a hard object and thereby limit the depth at which the cutting edge cuts into the hard object. In use, when the cutting edge cuts into a hard object, the depth stop engages the hard object to limit the cutting depth.

18 Claims, 6 Drawing Sheets

(56) References Cited

U.S. PATENT DOCUMENTS

| | | |
|---|---|---|
| 2,850,007 A | 9/1958 | Lingley |
| 3,064,651 A | 11/1960 | Henderson |
| 3,082,805 A | 3/1963 | Royce |
| 3,320,957 A | 5/1967 | Sokolik |
| 3,614,953 A | 10/1971 | Moss |
| 3,683,891 A | 8/1972 | Eskridge et al. |
| 3,705,577 A | 12/1972 | Sierra |
| 3,732,858 A | 5/1973 | Banko |
| 3,749,085 A | 7/1973 | Wilson et al. |
| 3,800,783 A | 4/1974 | Jamshidi |
| 3,815,604 A | 6/1974 | O'Malley et al. |
| 3,831,585 A | 8/1974 | Brondy et al. |
| 3,837,345 A | 9/1974 | Matar |
| 3,845,375 A | 10/1974 | Stiebel |
| 3,937,222 A | 2/1976 | Banko |
| 3,945,375 A | 3/1976 | Banko |
| 3,976,077 A | 8/1976 | Kerfoot, Jr. |
| 3,995,619 A | 12/1976 | Glatzer |
| 4,007,732 A | 2/1977 | Kvavle et al. |
| 4,020,847 A | 5/1977 | Clark, III |
| 4,030,503 A | 6/1977 | Clark, III |
| 4,034,744 A | 7/1977 | Goldberg |
| 4,038,985 A | 8/1977 | Chiulli |
| 4,112,708 A | 9/1978 | Fukuda |
| 4,177,797 A | 12/1979 | Baylis et al. |
| 4,210,146 A | 7/1980 | Banko |
| 4,273,128 A | 6/1981 | Lary |
| 4,306,562 A | 12/1981 | Osborne |
| 4,306,570 A | 12/1981 | Matthews |
| 4,349,032 A | 9/1982 | Koyata |
| 4,368,730 A | 1/1983 | Sharrock |
| 4,424,045 A | 1/1984 | Kulischenko et al. |
| 4,436,091 A | 3/1984 | Banko |
| 4,445,509 A | 5/1984 | Auth |
| 4,490,139 A | 12/1984 | Huizenga et al. |
| 4,494,057 A | 1/1985 | Hotta |
| 4,512,344 A | 4/1985 | Barber |
| 4,589,412 A | 5/1986 | Kensey |
| 4,603,694 A | 8/1986 | Wheeler |
| 4,620,547 A | 11/1986 | Boebel |
| 4,631,052 A | 12/1986 | Kensey |
| 4,646,719 A | 3/1987 | Neuman et al. |
| 4,646,736 A | 3/1987 | Auth |
| 4,646,738 A | 3/1987 | Trott |
| 4,649,919 A | 3/1987 | Thimsen et al. |
| 4,653,496 A | 3/1987 | Bundy et al. |
| 4,664,112 A | 5/1987 | Kensey et al. |
| 4,669,469 A | 6/1987 | Gifford, III et al. |
| 4,679,558 A | 7/1987 | Kensey et al. |
| 4,686,982 A | 8/1987 | Nash |
| 4,692,141 A | 9/1987 | Mahurkar |
| 4,696,298 A | 9/1987 | Higgins et al. |
| 4,696,667 A | 9/1987 | Masch |
| 4,705,038 A | 11/1987 | Sjostrom |
| 4,706,671 A | 11/1987 | Weinrib |
| 4,728,319 A | 3/1988 | Masch |
| 4,729,763 A | 3/1988 | Henrie |
| 4,730,616 A | 3/1988 | Frisbie et al. |
| 4,732,154 A | 3/1988 | Shiber |
| 4,733,662 A | 3/1988 | DeSatnick et al. |
| 4,745,919 A | 5/1988 | Bundey et al. |
| 4,747,406 A | 5/1988 | Nash |
| 4,747,821 A | 5/1988 | Kensey et al. |
| 4,749,376 A | 6/1988 | Kensey et al. |
| 4,754,755 A | 7/1988 | Husted |
| 4,757,819 A | 7/1988 | Yokoi et al. |
| 4,765,332 A * | 8/1988 | Fischell ............ A61B 17/32075 606/159 |
| 4,771,774 A | 9/1988 | Simpson et al. |
| 4,781,186 A | 11/1988 | Simpson et al. |
| 4,784,636 A | 11/1988 | Rydell |
| 4,790,812 A | 12/1988 | Hawkins, Jr. et al. |
| 4,794,931 A | 1/1989 | Yock |
| 4,817,613 A | 4/1989 | Jaraczewski et al. |
| 4,819,634 A | 4/1989 | Shiber |
| 4,819,635 A | 4/1989 | Shapiro |
| 4,838,268 A | 6/1989 | Keith et al. |
| 4,842,579 A | 6/1989 | Shiber |
| 4,844,064 A | 7/1989 | Thimsen et al. |
| 4,848,343 A | 7/1989 | Wallsten et al. |
| 4,850,957 A | 7/1989 | Summers |
| 4,857,046 A | 8/1989 | Stevens et al. |
| 4,867,157 A | 9/1989 | McGurk-Burleson et al. |
| 4,870,953 A | 10/1989 | DonMicheal et al. |
| 4,883,458 A | 11/1989 | Shiber |
| 4,886,061 A | 12/1989 | Fischell et al. |
| 4,886,490 A | 12/1989 | Shiber |
| 4,887,613 A | 12/1989 | Farr et al. |
| 4,894,051 A | 1/1990 | Shiber |
| 4,899,757 A | 2/1990 | Pope, Jr. et al. |
| 4,919,133 A | 4/1990 | Chiang |
| 4,923,462 A | 5/1990 | Stevens |
| 4,926,858 A | 5/1990 | Gifford, III et al. |
| 4,928,693 A | 5/1990 | Goodin et al. |
| 4,936,987 A | 6/1990 | Persinksi et al. |
| RE33,258 E | 7/1990 | Onik et al. |
| 4,950,238 A | 8/1990 | Sullivan |
| 4,954,338 A | 9/1990 | Mattox |
| 4,957,482 A | 9/1990 | Shiber |
| 4,966,604 A | 10/1990 | Reiss |
| 4,973,409 A | 11/1990 | Cook |
| 4,979,939 A | 12/1990 | Shiber |
| 4,979,951 A | 12/1990 | Simpson |
| 4,986,807 A | 1/1991 | Farr |
| 4,990,134 A | 2/1991 | Auth |
| 4,994,067 A | 2/1991 | Summers |
| 4,997,435 A | 3/1991 | Demeter |
| 5,000,185 A | 3/1991 | Yock |
| 5,002,553 A | 3/1991 | Shiber |
| 5,003,918 A | 4/1991 | Olson et al. |
| 5,007,896 A | 4/1991 | Shiber |
| 5,009,659 A | 4/1991 | Hamlin et al. |
| 5,019,088 A | 5/1991 | Farr |
| 5,024,234 A | 6/1991 | Leary et al. |
| 5,024,651 A | 6/1991 | Shiber |
| 5,026,384 A | 6/1991 | Farr et al. |
| 5,029,588 A | 7/1991 | Yock et al. |
| 5,030,201 A | 7/1991 | Palestrant |
| 5,047,040 A | 9/1991 | Simpson et al. |
| 5,049,124 A | 9/1991 | Bales, Jr. |
| 5,053,044 A | 10/1991 | Mueller et al. |
| 5,054,492 A | 10/1991 | Scribner et al. |
| 5,064,435 A | 11/1991 | Porter |
| 5,071,425 A | 12/1991 | Gifford et al. |
| 5,074,841 A | 12/1991 | Ademovic et al. |
| 5,077,506 A | 12/1991 | Krause et al. |
| 5,078,722 A | 1/1992 | Stevens |
| 5,078,723 A | 1/1992 | Stevens |
| 5,084,010 A | 1/1992 | Plaia et al. |
| 5,085,662 A | 2/1992 | Willard |
| 5,087,265 A | 2/1992 | Summers |
| 5,092,839 A | 3/1992 | Kipperman |
| 5,092,873 A | 3/1992 | Simpson et al. |
| 5,095,911 A | 3/1992 | Pomeranz |
| 5,100,423 A | 3/1992 | Fearnot |
| 5,100,424 A | 3/1992 | Jang et al. |
| 5,100,426 A | 3/1992 | Nixon |
| 5,110,822 A | 5/1992 | Sherba et al. |
| 5,112,345 A | 5/1992 | Farr |
| 5,114,399 A | 5/1992 | Kovalcheck |
| 5,115,814 A | 5/1992 | Griffith et al. |
| 5,120,323 A | 6/1992 | Shockey et al. |
| 5,127,902 A | 7/1992 | Fischell |
| 5,127,917 A | 7/1992 | Niederhauser et al. |
| 5,135,531 A | 8/1992 | Shiber |
| 5,154,705 A | 10/1992 | Fleischhacker et al. |
| 5,154,724 A | 10/1992 | Andrews |
| 5,165,421 A | 11/1992 | Fleischhacker et al. |
| 5,176,693 A | 1/1993 | Pannek, Jr. |
| 5,178,625 A | 1/1993 | Groshong |
| 5,181,920 A | 1/1993 | Mueller et al. |
| 5,183,432 A | 2/1993 | Noguchi |
| 5,190,528 A | 3/1993 | Fonger et al. |
| 5,192,291 A | 3/1993 | Pannek, Jr. |

(56) References Cited

U.S. PATENT DOCUMENTS

| | | |
|---|---|---|
| 5,195,956 A | 3/1993 | Stockmeier |
| 5,211,651 A | 5/1993 | Reger et al. |
| 5,217,474 A | 6/1993 | Zacca et al. |
| 5,222,966 A | 6/1993 | Perkins et al. |
| 5,224,488 A | 7/1993 | Neuffer |
| 5,224,945 A | 7/1993 | Pannek, Jr. |
| 5,224,949 A | 7/1993 | Gomringer et al. |
| 5,226,909 A | 7/1993 | Evans et al. |
| 5,226,910 A | 7/1993 | Kajiyama et al. |
| 5,234,451 A | 8/1993 | Osypka |
| 5,242,460 A | 9/1993 | Klein et al. |
| 5,242,461 A | 9/1993 | Kortenbach et al. |
| 5,250,059 A | 10/1993 | Andreas et al. |
| 5,250,065 A | 10/1993 | Clement et al. |
| 5,263,928 A | 11/1993 | Trauthen et al. |
| 5,263,959 A | 11/1993 | Fischell |
| 5,267,955 A | 12/1993 | Hanson |
| 5,267,982 A | 12/1993 | Sylvanowicz |
| 5,269,793 A | 12/1993 | Simpson et al. |
| 5,273,526 A | 12/1993 | Dance et al. |
| 5,282,484 A | 2/1994 | Reger |
| 5,284,486 A | 2/1994 | Kotula et al. |
| 5,285,795 A | 2/1994 | Ryan et al. |
| 5,295,493 A | 3/1994 | Radisch, Jr. |
| 5,300,085 A | 4/1994 | Yock |
| 5,306,294 A | 4/1994 | Winston et al. |
| 5,308,354 A | 5/1994 | Zacca et al. |
| 5,312,425 A | 5/1994 | Evans et al. |
| 5,312,427 A | 5/1994 | Shturman |
| 5,314,438 A | 5/1994 | Shturman |
| 5,318,032 A | 6/1994 | Lonsbury et al. |
| 5,318,528 A | 6/1994 | Heaven et al. |
| 5,318,576 A | 6/1994 | Plassche, Jr. et al. |
| 5,321,501 A | 6/1994 | Swanson et al. |
| 5,322,508 A | 6/1994 | Viera |
| 5,350,390 A | 9/1994 | Sher |
| 5,356,418 A | 10/1994 | Shturman |
| 5,358,472 A | 10/1994 | Vance et al. |
| 5,358,485 A | 10/1994 | Vance et al. |
| 5,360,432 A | 11/1994 | Shturman |
| 5,366,463 A | 11/1994 | Ryan |
| 5,368,035 A | 11/1994 | Hamm et al. |
| 5,370,609 A | 12/1994 | Drasler et al. |
| 5,370,651 A | 12/1994 | Summers |
| 5,372,601 A | 12/1994 | Lary |
| 5,372,602 A | 12/1994 | Burke |
| 5,373,619 A | 12/1994 | Fleischhacker et al. |
| 5,373,849 A | 12/1994 | Maroney et al. |
| 5,377,682 A | 1/1995 | Ueno et al. |
| 5,378,234 A | 1/1995 | Hammerslag et al. |
| 5,383,460 A | 1/1995 | Jang et al. |
| 5,395,311 A | 3/1995 | Andrews |
| 5,395,313 A | 3/1995 | Naves et al. |
| 5,395,335 A | 3/1995 | Jang |
| 5,397,345 A | 3/1995 | Lazarus |
| 5,402,790 A | 4/1995 | Jang et al. |
| 5,403,334 A | 4/1995 | Evans et al. |
| 5,409,454 A | 4/1995 | Fischell et al. |
| 5,413,107 A | 5/1995 | Oakley et al. |
| 5,419,774 A | 5/1995 | Willard et al. |
| 5,423,740 A | 6/1995 | Sullivan |
| 5,423,799 A | 6/1995 | Shiu |
| 5,423,838 A | 6/1995 | Willard |
| 5,423,846 A | 6/1995 | Fischell |
| 5,427,107 A | 6/1995 | Milo et al. |
| 5,429,136 A | 7/1995 | Milo et al. |
| 5,431,673 A | 7/1995 | Summers et al. |
| 5,441,510 A | 8/1995 | Simpson et al. |
| 5,443,446 A | 8/1995 | Shturman |
| 5,443,497 A | 8/1995 | Venbrux |
| 5,444,078 A | 8/1995 | Yu et al. |
| 5,445,155 A | 8/1995 | Sieben |
| 5,449,369 A | 9/1995 | Imran |
| 5,451,233 A | 9/1995 | Yock |
| 5,454,809 A | 10/1995 | Janssen |
| 5,456,667 A | 10/1995 | Ham et al. |
| 5,456,689 A | 10/1995 | Kresch et al. |
| 5,458,585 A | 10/1995 | Salmon et al. |
| 5,459,570 A | 10/1995 | Swanson et al. |
| 5,464,016 A | 11/1995 | Nicholas et al. |
| 5,470,415 A | 11/1995 | Perkins et al. |
| 5,485,042 A | 1/1996 | Burke et al. |
| 5,485,840 A | 1/1996 | Bauman |
| 5,487,729 A | 1/1996 | Avellanet et al. |
| 5,489,295 A | 2/1996 | Piplani et al. |
| 5,491,524 A | 2/1996 | Hellmuth et al. |
| 5,496,267 A | 3/1996 | Drasler et al. |
| 5,501,694 A | 3/1996 | Ressemann et al. |
| 5,503,155 A | 4/1996 | Salmon et al. |
| 5,505,210 A | 4/1996 | Clement |
| 5,507,292 A | 4/1996 | Jang et al. |
| 5,507,760 A | 4/1996 | Wynne et al. |
| 5,507,761 A | 4/1996 | Duer |
| 5,507,795 A | 4/1996 | Chiang et al. |
| 5,512,044 A | 4/1996 | Duer |
| 5,514,115 A | 5/1996 | Frantzen et al. |
| 5,520,189 A | 5/1996 | Malinowski et al. |
| 5,522,825 A | 6/1996 | Kropf et al. |
| 5,522,880 A | 6/1996 | Barone et al. |
| 5,527,292 A | 6/1996 | Adams et al. |
| 5,527,298 A | 6/1996 | Vance et al. |
| 5,527,325 A | 6/1996 | Conley et al. |
| 5,531,685 A | 7/1996 | Hemmer et al. |
| 5,531,690 A | 7/1996 | Solar |
| 5,531,700 A | 7/1996 | Moore et al. |
| 5,540,707 A | 7/1996 | Ressemann et al. |
| 5,549,601 A | 8/1996 | McIntyre et al. |
| 5,554,163 A | 9/1996 | Shturman |
| 5,556,408 A | 9/1996 | Farhat |
| 5,558,093 A | 9/1996 | Pomeranz |
| 5,562,726 A | 10/1996 | Chuter |
| 5,562,728 A | 10/1996 | Lazarus et al. |
| 5,569,275 A | 10/1996 | Kotula et al. |
| 5,569,276 A | 10/1996 | Jang et al. |
| 5,569,277 A | 10/1996 | Evans et al. |
| 5,569,279 A | 10/1996 | Rainin |
| 5,570,693 A | 11/1996 | Jang et al. |
| 5,571,122 A | 11/1996 | Kelly et al. |
| 5,571,130 A | 11/1996 | Simpson et al. |
| 5,575,817 A | 11/1996 | Martin |
| 5,584,842 A | 12/1996 | Fogarty et al. |
| 5,584,843 A | 12/1996 | Wulfman et al. |
| 5,609,605 A | 3/1997 | Marshall et al. |
| 5,618,293 A | 4/1997 | Sample et al. |
| 5,620,447 A | 4/1997 | Smith et al. |
| 5,624,457 A | 4/1997 | Farley et al. |
| 5,626,562 A | 5/1997 | Castro |
| 5,626,576 A | 5/1997 | Janssen |
| 5,628,761 A | 5/1997 | Rizik |
| 5,632,754 A | 5/1997 | Farley et al. |
| 5,632,755 A | 5/1997 | Nordgren et al. |
| 5,634,464 A | 6/1997 | Jang et al. |
| 5,643,296 A | 7/1997 | Hundertmark et al. |
| 5,643,298 A | 7/1997 | Nordgren et al. |
| 5,649,941 A | 7/1997 | Lary |
| 5,660,180 A | 8/1997 | Malinowski et al. |
| 5,662,671 A | 9/1997 | Barbut et al. |
| 5,665,098 A | 9/1997 | Kelly et al. |
| 5,669,920 A | 9/1997 | Conley et al. |
| 5,674,232 A | 10/1997 | Halliburton |
| 5,676,696 A | 10/1997 | Marcade |
| 5,676,697 A | 10/1997 | McDonald |
| 5,681,336 A | 10/1997 | Clement et al. |
| 5,682,897 A | 11/1997 | Pomeranz |
| 5,683,449 A | 11/1997 | Marcade |
| 5,683,453 A | 11/1997 | Palmaz |
| 5,688,234 A | 11/1997 | Frisbie |
| 5,695,506 A | 12/1997 | Pike |
| 5,695,507 A | 12/1997 | Auth et al. |
| 5,697,944 A | 12/1997 | Lary |
| 5,700,240 A | 12/1997 | Barwick, Jr. et al. |
| 5,700,687 A | 12/1997 | Finn |
| 5,707,350 A | 1/1998 | Krause et al. |
| 5,707,376 A | 1/1998 | Kavteladze et al. |

(56) References Cited

U.S. PATENT DOCUMENTS

| | | |
|---|---|---|
| 5,707,383 A | 1/1998 | Bays et al. |
| 5,709,698 A | 1/1998 | Adams et al. |
| 5,713,913 A | 2/1998 | Lary et al. |
| 5,715,825 A | 2/1998 | Crowley |
| 5,716,410 A | 2/1998 | Wang et al. |
| 5,720,735 A | 2/1998 | Dorros |
| 5,724,977 A | 3/1998 | Yock et al. |
| 5,728,123 A | 3/1998 | Lemelson et al. |
| 5,733,296 A | 3/1998 | Rogers et al. |
| 5,735,816 A | 4/1998 | Lieber et al. |
| 5,741,270 A | 4/1998 | Hansen et al. |
| 5,766,192 A | 6/1998 | Zacca |
| 5,772,674 A | 6/1998 | Nakhjavan |
| 5,775,327 A | 7/1998 | Randolph et al. |
| 5,776,114 A | 7/1998 | Frantzen et al. |
| 5,776,153 A | 7/1998 | Rees |
| 5,779,643 A | 7/1998 | Lum et al. |
| 5,779,673 A | 7/1998 | Roth et al. |
| 5,779,721 A | 7/1998 | Nash |
| 5,779,722 A | 7/1998 | Shturman et al. |
| 5,792,157 A | 8/1998 | Mische et al. |
| 5,797,949 A | 8/1998 | Parodi |
| 5,799,655 A | 9/1998 | Jang et al. |
| 5,807,329 A | 9/1998 | Gelman |
| 5,810,867 A | 9/1998 | Zarbatany et al. |
| 5,816,923 A | 10/1998 | Milo et al. |
| 5,820,592 A | 10/1998 | Hammerslag |
| 5,823,971 A | 10/1998 | Robinson et al. |
| 5,824,039 A | 10/1998 | Piplani et al. |
| 5,824,055 A | 10/1998 | Spiridigliozzi et al. |
| 5,827,201 A | 10/1998 | Samson et al. |
| 5,827,229 A | 10/1998 | Auth et al. |
| 5,827,304 A | 10/1998 | Hart |
| 5,827,322 A | 10/1998 | Williams |
| 5,830,224 A | 11/1998 | Cohn et al. |
| 5,836,957 A | 11/1998 | Schulz et al. |
| 5,843,022 A | 12/1998 | Willard et al. |
| 5,843,103 A | 12/1998 | Wulfman |
| 5,843,161 A | 12/1998 | Solovay |
| 5,855,563 A | 1/1999 | Kaplan et al. |
| 5,865,748 A | 2/1999 | Co et al. |
| 5,868,685 A | 2/1999 | Powell et al. |
| 5,868,767 A | 2/1999 | Farley et al. |
| 5,871,536 A | 2/1999 | Lazarus |
| 5,873,882 A | 2/1999 | Straub et al. |
| 5,876,414 A | 3/1999 | Straub |
| 5,879,397 A | 3/1999 | Kalberer et al. |
| 5,883,458 A | 3/1999 | Sumita et al. |
| 5,888,201 A | 3/1999 | Stinson et al. |
| 5,895,399 A | 4/1999 | Barbut et al. |
| 5,895,402 A | 4/1999 | Hundertmark et al. |
| 5,902,245 A | 5/1999 | Yock |
| 5,910,150 A | 6/1999 | Saadat |
| 5,911,734 A | 6/1999 | Tsugita et al. |
| 5,916,210 A | 6/1999 | Winston |
| 5,922,003 A | 7/1999 | Anctil et al. |
| 5,935,108 A | 8/1999 | Katoh et al. |
| 5,938,645 A | 8/1999 | Gordon |
| 5,938,671 A | 8/1999 | Katoh et al. |
| 5,938,672 A | 8/1999 | Nash |
| 5,941,869 A | 8/1999 | Patterson et al. |
| 5,947,985 A | 9/1999 | Imran |
| 5,948,184 A | 9/1999 | Frantzen et al. |
| 5,951,480 A | 9/1999 | White et al. |
| 5,951,482 A | 9/1999 | Winston et al. |
| 5,954,745 A | 9/1999 | Gertler et al. |
| 5,968,064 A | 10/1999 | Selmon et al. |
| 5,972,019 A | 10/1999 | Engelson et al. |
| 5,985,397 A | 11/1999 | Witt et al. |
| 5,989,281 A | 11/1999 | Barbut et al. |
| 5,997,557 A | 12/1999 | Barbut et al. |
| 6,001,112 A | 12/1999 | Taylor |
| 6,010,449 A | 1/2000 | Selmon et al. |
| 6,010,522 A | 1/2000 | Barbut et al. |
| 6,013,072 A | 1/2000 | Winston et al. |
| 6,019,778 A | 2/2000 | Wilson et al. |
| 6,022,362 A | 2/2000 | Lee et al. |
| 6,027,450 A | 2/2000 | Brown et al. |
| 6,027,460 A | 2/2000 | Shturman |
| 6,027,514 A | 2/2000 | Stine et al. |
| 6,032,673 A | 3/2000 | Savage et al. |
| 6,036,646 A | 3/2000 | Barthe et al. |
| 6,036,656 A | 3/2000 | Slater |
| 6,036,707 A | 3/2000 | Spaulding |
| 6,039,693 A | 3/2000 | Seward et al. |
| 6,048,349 A | 4/2000 | Winston et al. |
| 6,050,949 A | 4/2000 | White et al. |
| 6,063,093 A | 5/2000 | Winston et al. |
| 6,066,153 A | 5/2000 | Lev |
| 6,068,603 A | 5/2000 | Suzuki |
| 6,068,638 A | 5/2000 | Makower |
| 6,081,738 A | 6/2000 | Hinohara et al. |
| RE36,764 E | 7/2000 | Zacca et al. |
| 6,095,990 A | 8/2000 | Parodi |
| 6,099,542 A | 8/2000 | Cohn et al. |
| 6,106,515 A | 8/2000 | Winston et al. |
| 6,110,121 A | 8/2000 | Lenker |
| 6,120,515 A | 9/2000 | Rogers et al. |
| 6,120,516 A | 9/2000 | Selmon et al. |
| 6,126,649 A | 10/2000 | VanTassel et al. |
| 6,129,734 A | 10/2000 | Shturman et al. |
| 6,134,003 A | 10/2000 | Tearney et al. |
| 6,152,909 A | 11/2000 | Bagaoisan et al. |
| 6,152,938 A | 11/2000 | Curry |
| 6,156,046 A | 12/2000 | Passafaro et al. |
| 6,157,852 A | 12/2000 | Selmon et al. |
| 6,159,195 A | 12/2000 | Ha et al. |
| 6,159,225 A | 12/2000 | Makower |
| 6,165,127 A | 12/2000 | Crowley |
| 6,179,859 B1 | 1/2001 | Bates et al. |
| 6,183,432 B1 | 2/2001 | Milo |
| 6,187,025 B1 | 2/2001 | Machek |
| 6,190,353 B1 | 2/2001 | Makower et al. |
| 6,191,862 B1 | 2/2001 | Swanson et al. |
| 6,193,676 B1 | 2/2001 | Winston et al. |
| 6,196,963 B1 | 3/2001 | Williams |
| 6,206,898 B1 | 3/2001 | Honeycutt et al. |
| 6,217,527 B1 | 4/2001 | Selmon et al. |
| 6,217,549 B1 | 4/2001 | Selmon et al. |
| 6,217,595 B1 | 4/2001 | Shturman et al. |
| 6,221,049 B1 | 4/2001 | Selmon et al. |
| 6,221,332 B1 | 4/2001 | Thumm et al. |
| 6,228,049 B1 | 5/2001 | Schroeder et al. |
| 6,228,076 B1 | 5/2001 | Winston et al. |
| 6,231,546 B1 | 5/2001 | Milo et al. |
| 6,231,549 B1 | 5/2001 | Noecker et al. |
| 6,235,000 B1 | 5/2001 | Milo et al. |
| 6,238,405 B1 | 5/2001 | Findlay, III et al. |
| 6,241,667 B1 | 6/2001 | Vetter et al. |
| 6,241,744 B1 | 6/2001 | Imran et al. |
| 6,245,012 B1 | 6/2001 | Kleshinski |
| 6,258,052 B1 | 7/2001 | Milo |
| 6,263,236 B1 | 7/2001 | Kasinkas et al. |
| 6,264,611 B1 | 7/2001 | Ishikawa et al. |
| 6,266,550 B1 | 7/2001 | Selmon et al. |
| 6,277,138 B1 | 8/2001 | Levinson et al. |
| 6,283,951 B1 | 9/2001 | Flaherty et al. |
| 6,283,983 B1 | 9/2001 | Makower et al. |
| 6,299,622 B1 | 10/2001 | Snow et al. |
| 6,299,623 B1 | 10/2001 | Wulfman |
| 6,302,875 B1 | 10/2001 | Makower et al. |
| 6,305,834 B1 | 10/2001 | Schubert et al. |
| 6,312,444 B1 | 11/2001 | Barbut |
| 6,319,242 B1 | 11/2001 | Patterson et al. |
| 6,319,275 B1 | 11/2001 | Lashinski et al. |
| 6,330,884 B1 | 12/2001 | Kim |
| 6,355,005 B1 | 3/2002 | Powell et al. |
| 6,361,545 B1 | 3/2002 | Macoviak et al. |
| 6,375,615 B1 | 4/2002 | Flaherty et al. |
| 6,383,195 B1 | 5/2002 | Richard |
| 6,383,205 B1 | 5/2002 | Samson et al. |
| 6,394,976 B1 | 5/2002 | Winston et al. |
| 6,398,798 B2 | 6/2002 | Selmon et al. |
| 6,422,736 B1 | 7/2002 | Antonaides et al. |

(56) References Cited

U.S. PATENT DOCUMENTS

| | | |
|---|---|---|
| 6,423,081 B1 | 7/2002 | Lee et al. |
| 6,425,870 B1 | 7/2002 | Flesch |
| 6,428,551 B1 | 8/2002 | Hall et al. |
| 6,428,552 B1 | 8/2002 | Sparks |
| 6,443,966 B1 | 9/2002 | Shiu |
| 6,445,939 B1 | 9/2002 | Swanson et al. |
| 6,447,525 B2 | 9/2002 | Follmer et al. |
| 6,451,036 B1 | 9/2002 | Heitzmann et al. |
| 6,454,779 B1 | 9/2002 | Taylor |
| 6,475,226 B1 | 11/2002 | Belef et al. |
| 6,482,217 B1 | 11/2002 | Pintor et al. |
| 6,497,711 B1 | 12/2002 | Plaia et al. |
| 6,501,551 B1 | 12/2002 | Tearney et al. |
| 6,520,975 B2 | 2/2003 | Branco |
| RE38,018 E | 3/2003 | Anctil et al. |
| 6,532,380 B1 | 3/2003 | Close et al. |
| 6,533,749 B1 | 3/2003 | Mitusina et al. |
| 6,561,998 B1 | 5/2003 | Roth et al. |
| 6,565,588 B1 | 5/2003 | Clement et al. |
| 6,569,177 B1 | 5/2003 | Dillard et al. |
| 6,592,526 B1 | 7/2003 | Lenker |
| 6,620,180 B1 | 9/2003 | Bays et al. |
| 6,623,437 B2 | 9/2003 | Hinchliffe et al. |
| 6,623,495 B2 | 9/2003 | Findlay, III et al. |
| 6,623,496 B2 | 9/2003 | Snow et al. |
| 6,629,953 B1 | 10/2003 | Boyd |
| 6,638,233 B2 | 10/2003 | Corvi et al. |
| RE38,335 E | 11/2003 | Aust et al. |
| 6,652,505 B1 | 11/2003 | Tsugita |
| 6,652,548 B2 | 11/2003 | Evans et al. |
| 6,656,195 B2 | 12/2003 | Peters et al. |
| 6,666,874 B2 | 12/2003 | Heitzmann et al. |
| 6,682,543 B2 | 1/2004 | Barbut et al. |
| 6,733,511 B2 | 5/2004 | Hall et al. |
| 6,740,103 B2 | 5/2004 | Hall et al. |
| 6,746,462 B1 | 6/2004 | Selmon et al. |
| 6,764,495 B2 | 7/2004 | Lee et al. |
| 6,790,204 B2 | 9/2004 | Zadno-Azizi et al. |
| 6,790,215 B2 | 9/2004 | Findlay, III et al. |
| 6,818,001 B2 | 11/2004 | Wulfman et al. |
| 6,830,577 B2 | 12/2004 | Nash et al. |
| 6,843,797 B2 | 1/2005 | Nash et al. |
| 6,849,068 B1 | 2/2005 | Bagaoisan et al. |
| 6,863,676 B2 | 3/2005 | Lee et al. |
| 6,911,026 B1 | 6/2005 | Hall et al. |
| 6,970,732 B2 | 11/2005 | Winston et al. |
| 6,997,934 B2 | 2/2006 | Snow et al. |
| 7,153,315 B2 | 12/2006 | Miller |
| 7,172,610 B2 | 2/2007 | Heitzmann et al. |
| 7,208,511 B2 | 4/2007 | Williams et al. |
| 7,235,088 B2 | 6/2007 | Pintor et al. |
| 7,318,831 B2 | 1/2008 | Alvarez et al. |
| 7,388,495 B2 | 6/2008 | Fallin et al. |
| 7,479,148 B2 | 1/2009 | Beaupre |
| 7,488,322 B2 | 2/2009 | Brunnett et al. |
| 7,524,289 B2 | 4/2009 | Lenker |
| 7,603,166 B2 | 10/2009 | Casscells, III et al. |
| 7,708,749 B2 | 5/2010 | Simpson et al. |
| 7,713,235 B2 | 5/2010 | Torrance et al. |
| 7,713,279 B2 | 5/2010 | Simpson et al. |
| 7,729,745 B2 | 6/2010 | Maschke |
| 7,734,332 B2 | 6/2010 | Sher |
| 7,753,852 B2 | 7/2010 | Maschke |
| 7,758,599 B2 | 7/2010 | Snow et al. |
| 7,771,444 B2 | 8/2010 | Patel et al. |
| 7,887,556 B2 | 2/2011 | Simpson et al. |
| 2001/0000041 A1 | 3/2001 | Selmon et al. |
| 2001/0031784 A1 | 10/2001 | Petersen et al. |
| 2001/0031981 A1 | 10/2001 | Evans et al. |
| 2001/0044622 A1 | 11/2001 | Vardi et al. |
| 2001/0049500 A1 | 12/2001 | VanTassel et al. |
| 2002/0019644 A1 | 2/2002 | Hastings et al. |
| 2002/0022788 A1 | 2/2002 | Corvi et al. |
| 2002/0058904 A1 | 5/2002 | Boock et al. |
| 2002/0077373 A1 | 6/2002 | Hudson |
| 2002/0077642 A1 | 6/2002 | Patel et al. |
| 2002/0095141 A1 | 7/2002 | Belef et al. |
| 2002/0103459 A1 | 8/2002 | Sparks et al. |
| 2002/0177800 A1 | 11/2002 | Bagaoisan et al. |
| 2002/0188307 A1 | 12/2002 | Pintor et al. |
| 2003/0018346 A1 | 1/2003 | Follmer et al. |
| 2003/0023263 A1 | 1/2003 | Krolik et al. |
| 2003/0093098 A1 | 5/2003 | Heitzmann et al. |
| 2003/0120295 A1 | 6/2003 | Simpson et al. |
| 2003/0125757 A1 | 7/2003 | Patel et al. |
| 2003/0125758 A1 | 7/2003 | Simpson et al. |
| 2003/0163126 A1 | 8/2003 | West, Jr. |
| 2003/0199747 A1 | 10/2003 | Michlitsch et al. |
| 2003/0206484 A1 | 11/2003 | Childers et al. |
| 2003/0229369 A1 | 12/2003 | Findlay, III et al. |
| 2004/0006358 A1 | 1/2004 | Wulfman et al. |
| 2004/0049225 A1 | 3/2004 | Denison |
| 2004/0167553 A1 | 8/2004 | Simpson et al. |
| 2004/0167554 A1 | 8/2004 | Simpson et al. |
| 2004/0193034 A1 | 9/2004 | Wasicek et al. |
| 2004/0210245 A1 | 10/2004 | Erickson et al. |
| 2005/0004585 A1 | 1/2005 | Hall et al. |
| 2005/0004594 A1 | 1/2005 | Nool et al. |
| 2005/0021063 A1 | 1/2005 | Hall et al. |
| 2005/0042239 A1 | 2/2005 | Lipiecki et al. |
| 2005/0090845 A1 | 4/2005 | Boyd |
| 2005/0090849 A1 | 4/2005 | Adams |
| 2005/0177068 A1 | 8/2005 | Simpson |
| 2005/0216018 A1 | 9/2005 | Sennett |
| 2005/0222596 A1 | 10/2005 | Maschke |
| 2005/0222663 A1 | 10/2005 | Simpson et al. |
| 2006/0015126 A1 | 1/2006 | Sher |
| 2006/0235334 A1 | 10/2006 | Corvi et al. |
| 2006/0259052 A1 | 11/2006 | Pintor et al. |
| 2007/0010840 A1 | 1/2007 | Rosenthal et al. |
| 2007/0038061 A1 | 2/2007 | Huennekens et al. |
| 2007/0049958 A1 | 3/2007 | Adams |
| 2007/0135712 A1 | 6/2007 | Maschke |
| 2007/0135886 A1 | 6/2007 | Maschke |
| 2007/0167824 A1 | 7/2007 | Lee et al. |
| 2007/0225739 A1 | 9/2007 | Pintor et al. |
| 2007/0265647 A1 | 11/2007 | Bonnette et al. |
| 2007/0276419 A1 | 11/2007 | Rosenthal |
| 2008/0001643 A1 | 1/2008 | Lee |
| 2008/0004644 A1 | 1/2008 | To et al. |
| 2008/0004645 A1 | 1/2008 | To et al. |
| 2008/0004646 A1 | 1/2008 | To et al. |
| 2008/0004647 A1 | 1/2008 | To et al. |
| 2008/0045986 A1 | 2/2008 | To et al. |
| 2008/0051812 A1 | 2/2008 | Schmitz et al. |
| 2008/0065124 A1 | 3/2008 | Olson |
| 2008/0065125 A1 | 3/2008 | Olson |
| 2008/0097403 A1 | 4/2008 | Donaldson et al. |
| 2008/0125799 A1 | 5/2008 | Adams |
| 2008/0161840 A1 | 7/2008 | Osiroff et al. |
| 2008/0177139 A1 | 7/2008 | Courtney et al. |
| 2008/0208227 A1 | 8/2008 | Kadykowski et al. |
| 2008/0249553 A1 | 10/2008 | Gruber et al. |
| 2008/0312673 A1 | 12/2008 | Viswanathan et al. |
| 2009/0012548 A1 | 1/2009 | Thatcher et al. |
| 2009/0018565 A1 | 1/2009 | To et al. |
| 2009/0018566 A1 | 1/2009 | Escudero et al. |
| 2009/0138031 A1 | 5/2009 | Tsukernik |
| 2009/0187203 A1 | 7/2009 | Corvi et al. |
| 2009/0216125 A1 | 8/2009 | Lenker |
| 2009/0216180 A1 | 8/2009 | Lee et al. |
| 2009/0226063 A1 | 9/2009 | Rangwala et al. |
| 2009/0234378 A1 | 9/2009 | Escudero et al. |
| 2009/0270888 A1 | 10/2009 | Patel et al. |
| 2009/0270966 A1 | 11/2009 | Mitusina |
| 2009/0299394 A1 | 12/2009 | Simpson et al. |
| 2009/0306689 A1 | 12/2009 | Welty et al. |
| 2010/0030216 A1 | 2/2010 | Arcenio |
| 2010/0049225 A1 | 2/2010 | To et al. |
| 2010/0130996 A1 | 5/2010 | Doud et al. |
| 2010/0198240 A1 | 8/2010 | Simpson et al. |
| 2010/0241147 A1 | 9/2010 | Maschke |
| 2010/0280534 A1 | 11/2010 | Sher |
| 2010/0292721 A1 | 11/2010 | Moberg |

(56) References Cited

U.S. PATENT DOCUMENTS

| | | |
|---|---|---|
| 2010/0298850 A1 | 11/2010 | Snow et al. |
| 2010/0312263 A1 | 12/2010 | Moberg et al. |
| 2011/0004107 A1 | 1/2011 | Rosenthal et al. |
| 2011/0022069 A1 | 1/2011 | Mitusina |
| 2011/0040315 A1 | 2/2011 | To et al. |
| 2011/0130777 A1 | 6/2011 | Zhang et al. |
| 2011/0144673 A1 | 6/2011 | Zhang et al. |
| 2012/0109172 A1* | 5/2012 | Schmitz .............. A61B 17/16 606/170 |
| 2012/0191121 A1* | 7/2012 | Chen .............. A61B 10/0266 606/180 |

FOREIGN PATENT DOCUMENTS

| | | |
|---|---|---|
| DE | 8900059 U1 | 5/1989 |
| DE | 93 03 531 U1 | 7/1994 |
| DE | 44 44 166 A1 | 6/1996 |
| DE | 29722136 U1 | 5/1999 |
| EP | 0086048 A2 | 8/1983 |
| EP | 0 701 009 A2 | 5/1984 |
| EP | 0 229 620 A2 | 7/1987 |
| EP | 0291170 A1 | 11/1988 |
| EP | 0 302 701 A2 | 2/1989 |
| EP | 0330843 A1 | 9/1989 |
| EP | 0373927 A2 | 6/1990 |
| EP | 0421457 A1 | 4/1991 |
| EP | 0 431 752 A2 | 6/1991 |
| EP | 0448859 A2 | 10/1991 |
| EP | 0463798 A1 | 1/1992 |
| EP | 0 490 565 A1 | 6/1992 |
| EP | 0514810 A1 | 11/1992 |
| EP | 0 526 042 A1 | 2/1993 |
| EP | 0533320 A2 | 3/1993 |
| EP | 0 608 911 A1 | 8/1994 |
| EP | 0 608 912 A1 | 8/1994 |
| EP | 0 611 522 A1 | 8/1994 |
| EP | 0 648 414 B1 | 4/1995 |
| EP | 0657140 A1 | 6/1995 |
| EP | 0 680 695 B1 | 11/1998 |
| EP | 0983749 A2 | 3/2000 |
| EP | 1767159 A1 | 3/2007 |
| EP | 1875871 A2 | 1/2008 |
| GB | 2093353 A | 9/1982 |
| GB | 2 115 829 A | 9/1983 |
| GB | 2210965 A | 6/1989 |
| JP | 2-206452 A | 8/1990 |
| JP | 2271847 A | 11/1990 |
| JP | 3186256 A | 8/1991 |
| JP | 4200459 A | 7/1992 |
| JP | 5042162 A | 2/1993 |
| JP | 5056984 A | 3/1993 |
| JP | 5184679 A | 7/1993 |
| JP | 6269460 A | 9/1994 |
| JP | 7075611 B | 8/1995 |
| SU | 442795 A1 | 9/1974 |
| SU | 665908 A1 | 6/1979 |
| WO | WO 8906517 A1 | 7/1989 |
| WO | WO 92/07500 A2 | 5/1992 |
| WO | WO 9313716 A1 | 7/1993 |
| WO | WO 9313717 A1 | 7/1993 |
| WO | 199316642 A1 | 9/1993 |
| WO | WO 9521576 A1 | 8/1995 |
| WO | WO 9611648 A1 | 4/1996 |
| WO | WO 9746164 A1 | 12/1997 |
| WO | WO 9804199 A1 | 2/1998 |
| WO | WO 9824372 A1 | 6/1998 |
| WO | WO 99/39648 A1 | 8/1999 |
| WO | WO 9952454 A1 | 10/1999 |
| WO | 200030531 A1 | 6/2000 |
| WO | WO 00/54735 A1 | 9/2000 |
| WO | WO 00/62913 A1 | 10/2000 |
| WO | WO 00/68300 A1 | 11/2000 |
| WO | WO 00/72955 A1 | 12/2000 |
| WO | WO 01/15609 A1 | 3/2001 |
| WO | WO 01/19444 A1 | 3/2001 |
| WO | WO 0130433 A1 | 5/2001 |
| WO | WO 01/43857 A1 | 6/2001 |
| WO | WO 0143809 A1 | 6/2001 |
| WO | WO 02/16017 A2 | 2/2002 |
| WO | WO 02/45598 A2 | 6/2002 |
| WO | 2006058223 A2 | 6/2006 |
| WO | 2006066012 A2 | 6/2006 |

OTHER PUBLICATIONS

Judkins Left Coronary Catheter, posted: Feb. 19, 2009, [online], [retrieved on Mar. 29, 2011], retrieved from the Cardiophile MD using Internet website <URL:http://cardiophile.org/2009/02/judkins-left-coronary-catheter.html> (3 pages).

Huang et al., "Optical Coherence Tomography," Science, 254: 11788-1181 (1991).

Brezinski et al., "Optical Coherence Tomography for Optical Biopsy," Circulation, 93:1206-1213 (1996).

Brezinski et al., "Assessing Atherosclerotic Plaque Morphology: Comparison of Optical Coherence Tomography and High Frequency Intravascular Ultrasound," Heart, 77:397-403 (1997).

* cited by examiner

TISSUE-REMOVING CATHETER AND TISSUE-REMOVING ELEMENT WITH DEPTH STOP

FIELD OF THE DISCLOSURE

The present disclosure generally relates to a tissue-removing catheter and more particularly to a tissue-removing catheter having a tissue-removing element with a depth stop.

BACKGROUND OF THE DISCLOSURE

Tissue-removing catheters are used to remove unwanted tissue from the body. As an example, certain catheters remove unwanted material from a blood vessel to open the blood vessel and improve blood flow through the vessel. In some instances, fixed objects that are not to be removed, such as stents, are present in the vessel with the material that is to be removed.

SUMMARY OF THE DISCLOSURE

A tissue-removing catheter includes a tissue-removing element operably connected to a drive shaft for rotation of the tissue-removing element about an axis of rotation in a cutting direction. The tissue-removing element includes a cutting edge that extends around the axis of rotation and a depth stop that extends around the axis of rotation radially inward of the cutting edge relative to the axis of rotation. The depth stop defines an engagement surface adapted to engage a hard object and thereby limit the depth at which the cutting edge cuts into the hard object. In use, when the cutting edge cuts into a hard object, the depth stop engages the hard object to limit the cutting depth.

Other features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
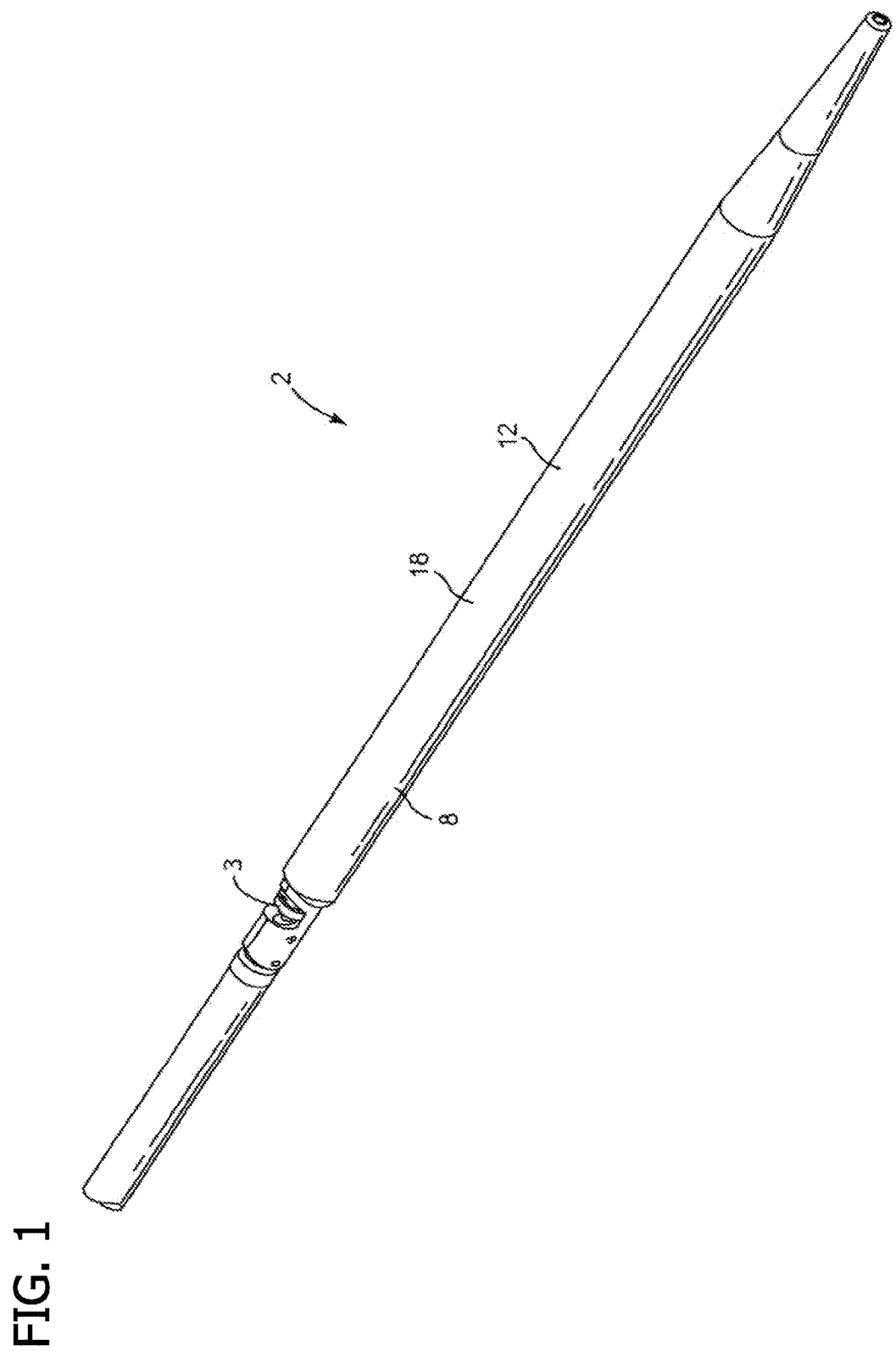
FIG. 1 is a perspective of a distal end of an atherectomy catheter.

Referring now to the drawings, a tissue-removing catheter for removing tissue from a body lumen is disclosed. In particular, the illustrated catheter is suitable for removing tissue from a body lumen wall, and is particularly suitable for removing (i.e., excising) soft tissue from a vessel wall (e.g., coronary arterial, peripheral arterial or peripheral venous wall). Features of the disclosed embodiments, however, may also be suitable for treating chronic total occlusion (CTO) of blood vessels, particularly coronary or peripheral arteries, and stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen. While the remaining discussion is directed toward catheters for removing tissue from and penetrating occlusions in blood vessels (e.g., atheromatous or thrombotic occlusive material in an artery, or other occlusions in veins), it will be appreciated that the teachings of the present disclosure apply equally to other types of tissue-removing catheters, including, but not limited to, catheters for penetrating and/or removing tissue from a variety of occlusive, stenotic, or hyperplastic material in a variety of body lumens.

Figure 2:
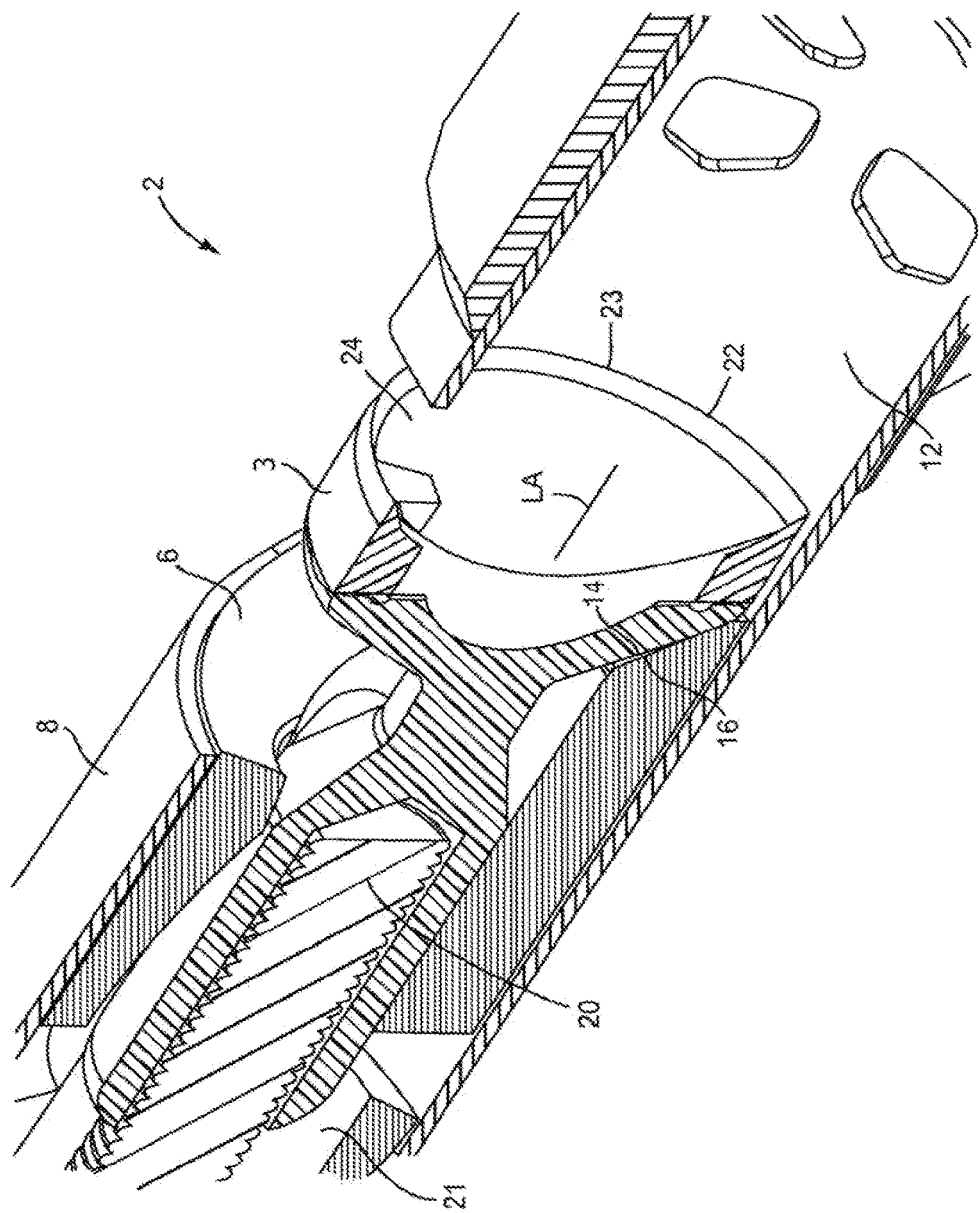
FIG. 2 is an enlarged fragmentary section of the atherectomy catheter of FIG. 1, illustrating one embodiment of a tissue-removing element in a stowed position.
Figure 3:
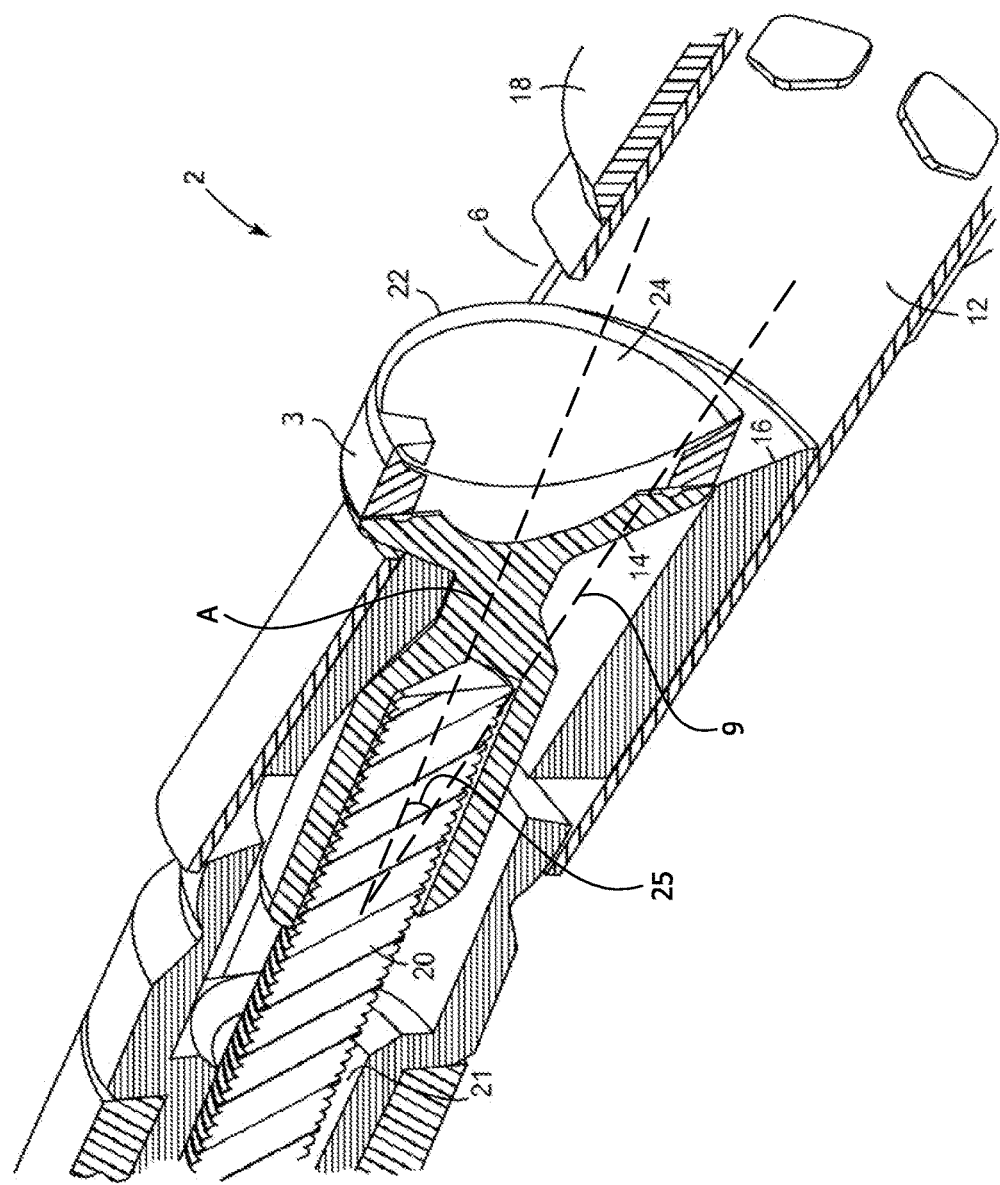
FIG. 3 is the enlarged fragmentary section of FIG. 1, illustrating the tissue-removing element in a deployed position.

Referring to FIGS. 1 to 3, an atherectomy catheter 2 (broadly, a "tissue-removing catheter"), which has a tissue-removing element 3 (broadly, a "tissue-removing element"), is used to cut material from a body lumen. The tissue-removing element 3 illustrated in FIGS. 1 to 3 is a conventional tissue-removing element. As will be explained below, tissue-removing element embodiments described in the present application are suitable replacements for the conventional tissue-removing element 3. That is, the tissue-removing element embodiments described herein below are suitable for use with the illustrated catheter 2 in place of the conventional tissue-removing element 3. The catheter 2 has an elongate body 8 having distal and proximal portions and sized and shaped for insertion into a body lumen of a subject. The tissue-removing element 3 is movable between a stored position (FIG. 2) and a cutting position (FIG. 3) relative to a window or opening 6 in the catheter body 8 adjacent the distal portion. The tissue-removing element 3 moves outwardly relative to the opening 6 so that an exposed portion of the element 3 extends outside the body 8 through the opening 6. The tissue-removing element 3 may be positioned relative to the body 8 and opening 6 so that less than 90 degrees of the tissue-removing element 3 is exposed to cut tissue. Of course, more of the tissue-removing element 3 may be exposed without departing from numerous aspects of the invention. Preferably, when the tissue-removing element 3 is in the cutting position, a longitudinal axis A of the tissue-removing element 3 is oriented at an attack angle 25 relative a longitudinal axis 9 of a leading portion of the catheter body 8.

Catheter 2 may have a maximum size of 3, 4, 5, 6, 7, 8, 9, 10, or 12 French (1, 1.3, 1.7, 2, 2.3, 2.7, 3, 3.3, or 4 mm) and may have a working length ranging of 20, 30, 40, 60, 80, 100, 120, 150, 180 or 210 cm depending on the requirements of the anatomical location in which use of the catheter is contemplated.

In the illustrated embodiment, the catheter 2 is moved distally through a vessel with the tissue-removing element 3 in the working or cutting position as described in further detail below. As the catheter 2 moves through the blood vessel, the tissue is cut by the tissue-removing element 3 and is directed into a tissue chamber 12 positioned distal to the tissue-removing element 3. The tissue chamber 12 may be somewhat elongate to accommodate the tissue that has been cut. It is understood that the catheter 2 may be configured to be moved proximally, rather than distally, within the body lumen in order to remove tissue. In such an embodiment, the tissue-removing element 3 would be oriented to face in the proximal direction, rather than the distal direction as illustrated. Accordingly, it is understood that the terms "distal" and "proximal" and the like used throughout the disclosure when referring to direction and relative locations of structures are not meant in a limiting sense, but are meant to apply to the embodiment as illustrated.

Referring to FIG. 3, the illustrated tissue-removing element 3 is moved proximally from the stored position so that a cam surface 14 on the tissue-removing element 3 engages a ramp 16 on the body 8 of the catheter 2. The interaction between the cam surface 14 and the ramp 16 causes the tissue-removing element 3 to move to the cutting position and also causes a tip 18 to deflect which tends to move the tissue-removing element 3 toward the tissue to be cut. The tissue-removing element 3 may be deployed in other ways without departing from the scope of the present invention.

The tissue-removing element 3 is coupled to a drive shaft 20 that extends through a lumen 21 in the catheter 2. The tissue-removing element 3 is rotated about an axis of rotation A in a rotational direction R when the drive shaft rotates about its longitudinal axis. The tissue-removing element 3 may be rotated at about 1 to 160,000 rpm in use but may be rotated at any other suitable speed depending upon the particular application. Other ways of driving rotation of the tissue-removing element 3 do not depart from the scope of the present invention.

Figure 4:
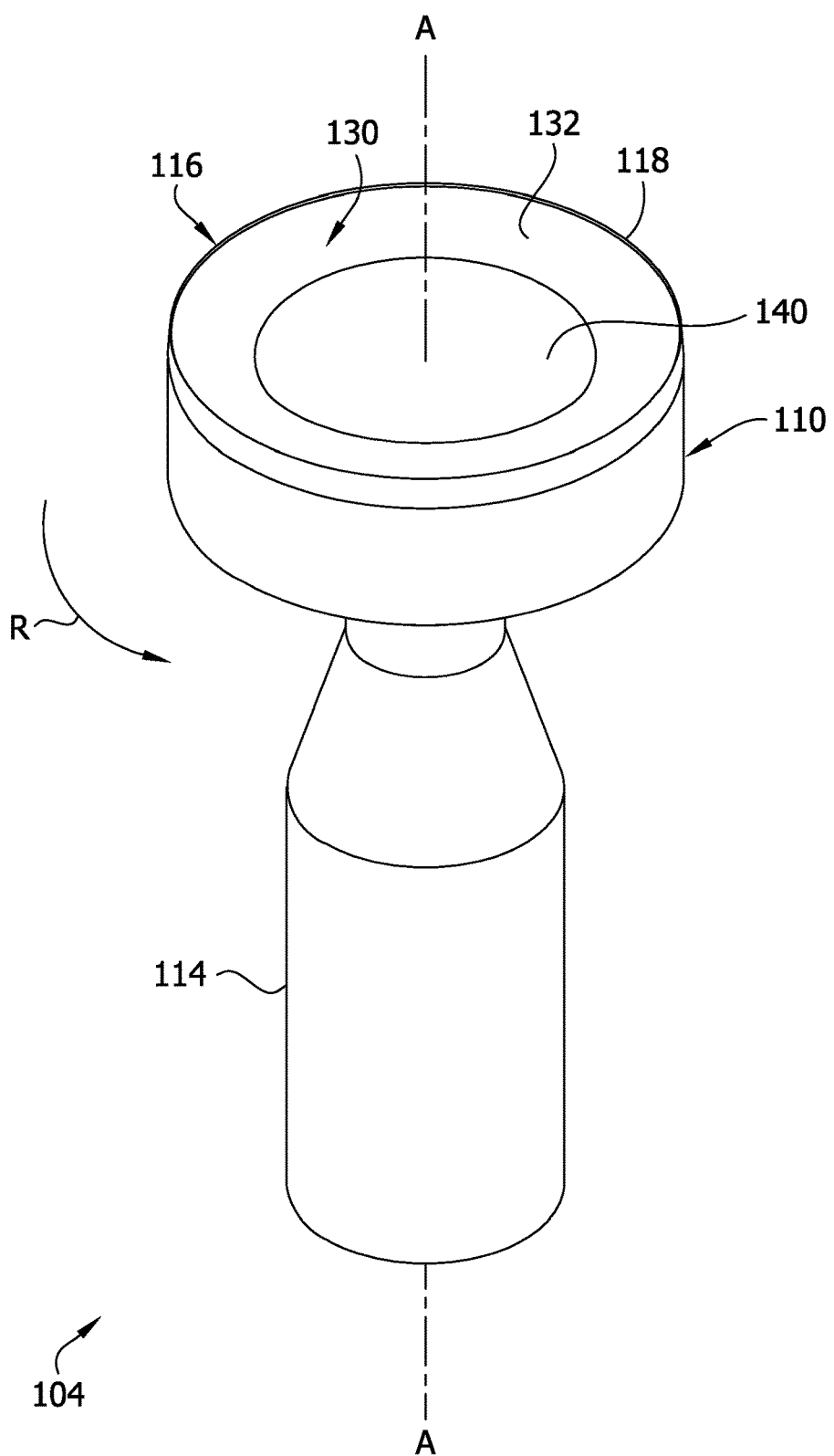
FIG. 4 is a perspective of another tissue-removing element.
Figure 5:
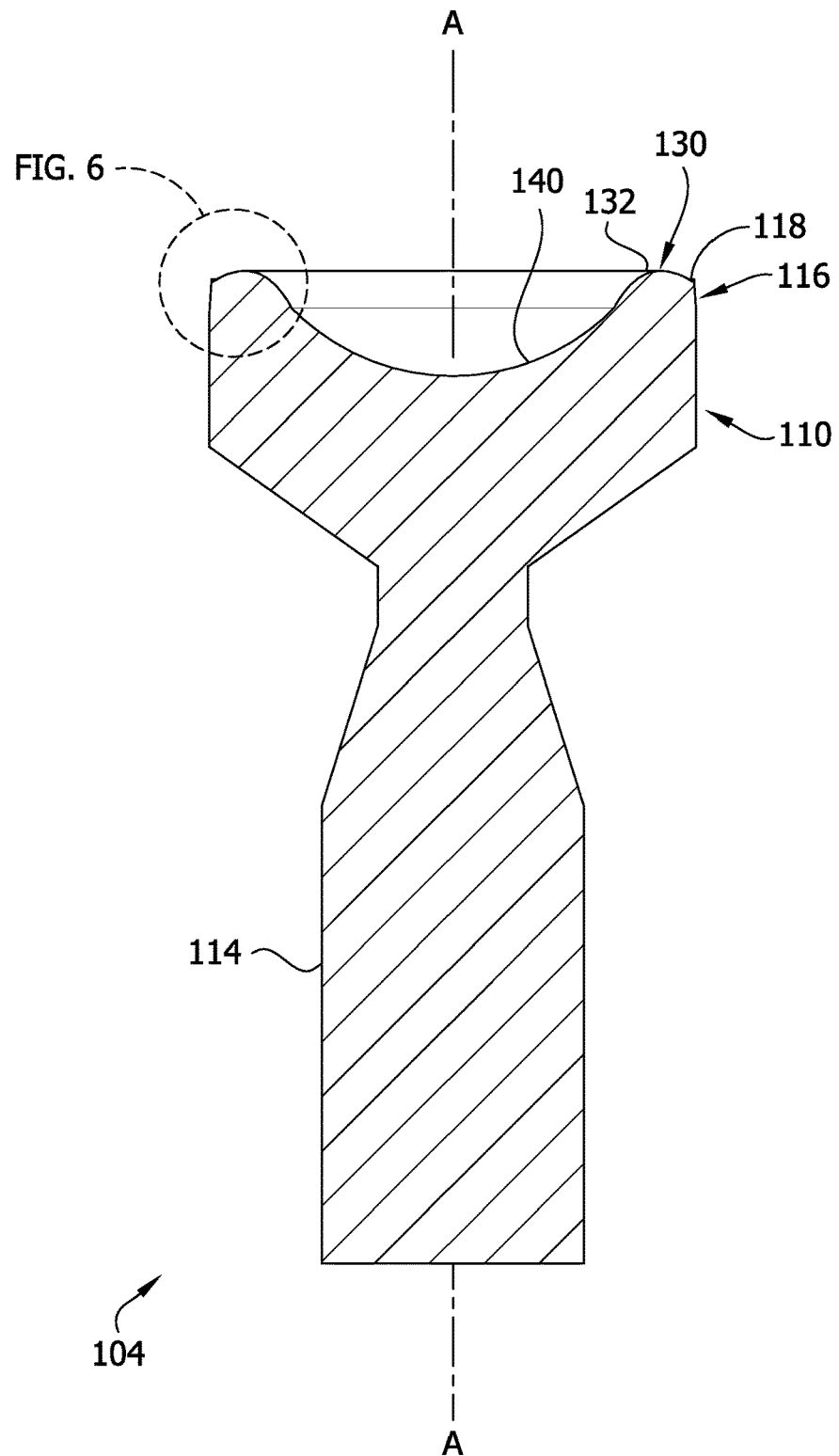
FIG. 5 is a section of the tissue-removing element of FIG. 4.

Referring to FIGS. 4 and 5, one embodiment of a tissue-removing element suitable for use with the catheter 2 is generally indicated at reference number 104. The tissue-removing element 104 comprises a tissue-removing element body having opposite proximal and distal axial ends (broadly, "first and second axial ends") and an axis of rotation A extending through the proximal and distal ends. The tissue-removing element 104 includes a tissue-removing head, generally indicated at reference numeral 110, at the distal axial end thereof. A stem 114 of the tissue-removing element 104 connects the tissue-removing element to the drive shaft 20 for rotation about the axis of rotation A in a cutting direction R. When the tissue-removing element 104 rotates in a body lumen, the tissue-removing head 110 is configured to cut tissue and thereby separate the tissue from the body lumen. As will be discussed in further detail below, the tissue-removing head 110 limits the depth of cuts the tissue-removing element 104 forms in hard material to minimize damage to certain hard objects, such as stents.

As shown in FIG. 5, in the illustrated embodiment, the tissue-removing element 104 is integrally formed of one piece of material. For example, the tissue-removing element 104 can be machined by removing material from a one-piece blank using a multi-axis mill, Swiss machine, electrical discharge machining, or other suitable manufacturing process. In other embodiments, it is contemplated that the tissue-removing element 104 can be a multi-piece assembly without departing from the scope of the invention. For example, in one or more embodiments, the tissue-removing element can comprise a two-piece assembly that includes a hard annular cutting blade that is fixedly mounted on a blank of softer material. In one or more embodiments, the one-piece tissue-removing element 104 can be made from one of M-4 steel, A-2 steel, CPM10V steel, CPM15V steel, 465 stainless steel, 17-4 stainless steel, MP35N alloy, 35N LT alloy, titanium, and blends thereof. Other materials, such as other types of tool steel, stainless steel, nickel, cobalt, chromium molybdenum, plastic, coated steels, or combinations thereof, can also be used without departing from the scope of the invention.

Figure 6:
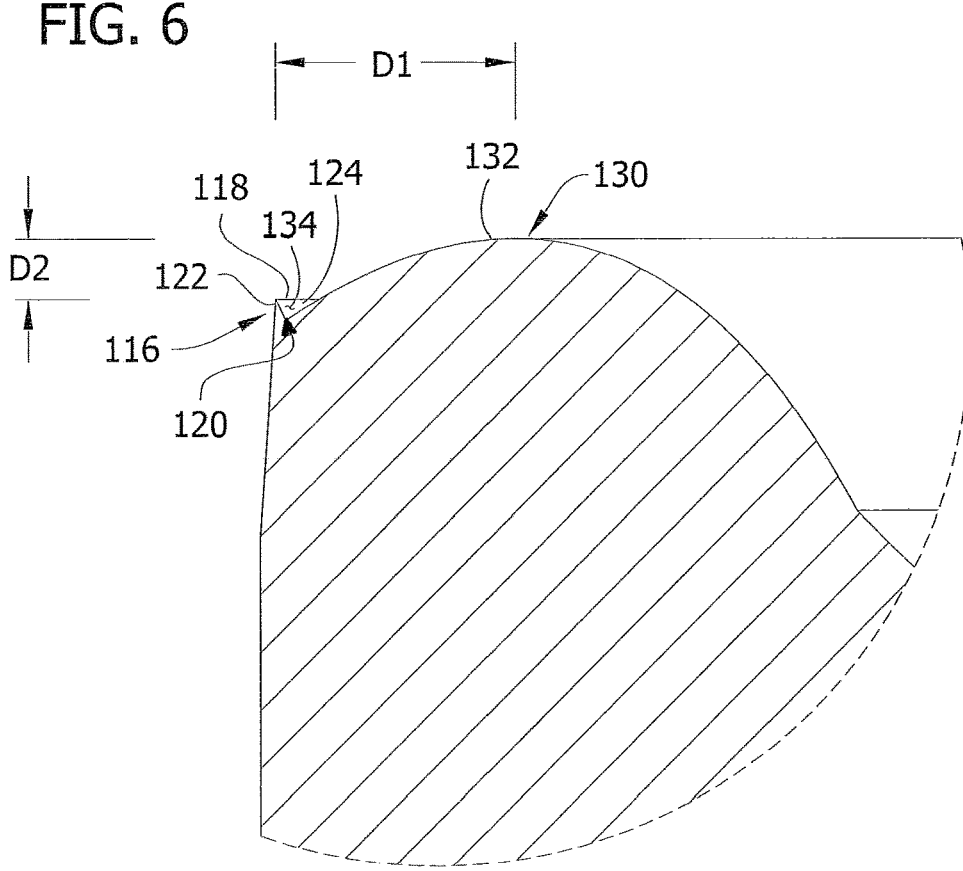
FIG. 6 is an enlarged view of a portion of FIG. 5.

As shown in FIGS. 4 and 6, the tissue-removing head 110 includes an annular cutting blade, generally indicated at 116, that extends around the axis of rotation A. The cutting blade 116 defines an annular cutting edge 118 at the first axial end of the tissue-removing element that extends around the axis of rotation A. In the illustrated embodiment, the cutting edge 118 is a continuous cutting edge. In other embodiments, the cutting edge could be discontinuous, such as where the cutting blade comprises cutting teeth or other spaced apart cutting formations, without departing from the scope of the invention. As shown in FIG. 6, the cutting blade 116 extends generally axially from a juncture 120. A radially outer blade surface 122 extends generally axially, and a beveled inner blade surface 124 extends at an angle relative to the outer blade surface. The beveled inner blade surface 124 intersects the radially outer blade surface 122 at the cutting edge 118.

Referring still to FIGS. 4 and 6, an annular depth stop, generally indicated at reference numeral 130, is formed in the tissue removing head 110 at the distal end of the tissue-removing element body 104. Like the cutting blade 116, the depth stop 130 extends around the axis of rotation A. In the illustrated embodiment, the depth stop 130 is substantially centered on (i.e., concentric with) the axis of rotation A. The depth stop 130 is also oriented substantially concentrically with the cutting blade 116 (i.e., the cutting blade is substantially centered on the axis of rotation A). The depth stop 130 is disposed radially inward of the cutting edge 118 relative to the axis of rotation A. The annular depth stop 130 has an engagement surface 132 at an axial end thereof that is configured to restrict a cutting depth of the annular cutting edge 118. When the cutting edge 118 forms a cut in a hard object that extends into the hard object a certain depth (e.g., a maximum cutting depth), the engagement surface 132 engages the object to prevent the cutting edge from cutting deeper into the object.

In the illustrated embodiment, the annular depth stop 130 has a uniform cross-sectional shape around the axis of rotation A. Referring to FIG. 5, in the illustrated embodiment the depth stop 130 defines an engagement surface 132 that has a generally convex cross-sectional shape. The engagement surface 132 has a smoothly curved shape that protrudes distally from the tissue-removing head 110. In other embodiments, the engagement surface can have other curved shapes or angular shapes without departing from the scope of the invention.

Referring to FIG. 6, the engagement surface 132 intersects the radially inner blade surface 124 at the juncture 120. The engagement surface 132 and the inner blade surface 124 extend away from the juncture 120 in radially opposite directions and the same axial direction. More specifically, the beveled inner blade surface 124 extends distally and radially outwardly from the juncture 120 at a substantially constant angle. A radially outer portion of the engagement surface 132 extends from the juncture 120 distally and radially inward toward the axis of rotation A to an apex at the axial end of the depth stop 130. The slope of the radially outer portion of the engagement surface 132 decreases as the surface approaches the apex. From the apex, a radially inner portion of the engagement surface 132 extends proximally and radially inward toward the axis of rotation A, increasing in slope as the surface extends inward away from the apex. Thus, the engagement surface 132 slopes radially outwardly and radially inwardly from the axial end of the depth stop 130. The radially outer portion of the engagement surface 132 and the inner blade surface 124 define an annular gap 134 therebetween. The gap 134 widens radially as it extends along the axis of rotation A in the distal direction from the juncture 120.

Figure 7:
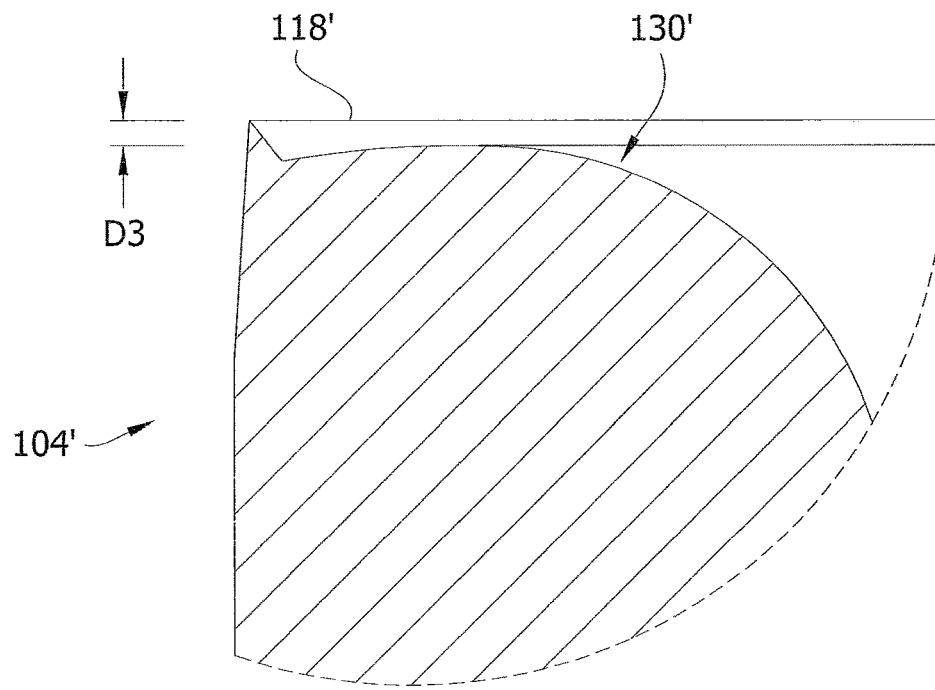
FIG. 7 is an enlarged section view similar to FIG. 7 of another embodiment of a tissue-removing element.

The axial end of the depth stop 130 is positioned relative the cutting edge 118 to restrict the cutting depth of the cutting edge. Referring to FIG. 6, the axial end of the depth stop 130 is spaced apart radially inward of the cutting edge 118 a distance D1. In one or more preferred embodiments, the axial end of the annular depth stop 130 is radially spaced apart from the cutting edge 118 a distance D1 of from about 0.0 inches (0.0 mm) to about 0.02 inches (0.508 mm), for example, from about 0.001 inches (0.0254 mm) to about 0.02 inches (0.508 mm). In the embodiment illustrated in FIGS. 4-6, the annular depth stop 130 protrudes axially beyond the cutting edge 118 in the distal direction. In one or more embodiments, the axial end of the depth stop 130 is axially spaced apart from the cutting edge 118 a distance D2 a distance of from about 0.0 inches (0.0 mm) to about 0.010 inches (0.254 mm), for example, from about 0.0005 inches (0.0127 mm) to about 0.010 inches (0.254 mm). Referring to FIG. 7, in another embodiment, a cutting edge 118' protrudes axially beyond the annular depth stop 130'. In one or more embodiments, the cutting edge 118' is axially spaced apart from the axial end of the depth stop 130' a distance D3 of from about 0.0 inches (0.0 mm) to about 0.010 inches (0.254 mm), for example, from about 0.0005 inches (0.0127 mm) to about 0.010 inches (0.254 mm). In still other embodiments (not shown), the cutting edge and the axial end of the annular depth stop are located at about the same axial location (i.e., within the same plane extending transversely relative to the axis A.

Referring again to FIG. 5, the illustrated tissue-removing head 110 is shaped and arranged to redirect cut tissue toward the tissue collection chamber 12. In the illustrated embodiment, the tissue-removing head 110 comprises a tissue-receiving depression 140. The tissue-receiving depression 140 is formed in the distal end of the tissue-removing element body 104 radially inward of the annular depth stop 130. In the illustrated embodiment, the tissue-receiving depression 140 is a concave depression centered on the axis of rotation A. There is a smoothly contoured transition from the engagement surface 132 of the depth stop 130 to the tissue-receiving depression 140. The tissue-receiving depression can have other shapes without departing from the scope of the invention. As the tissue-removing element 104 rotates in the cutting direction R and advances axially through the body lumen to remove tissue, the tissue is directed toward the center of the tissue-removing head 110. The tissue-receiving depression 140 receives the removed tissue and redirects the tissue toward the tissue-collection chamber 12. It will be understood that, other ways of directing removed tissue toward a tissue collection chamber can also be used without departing from the scope of the invention. Likewise, other tissue removal systems can also be used without departing from the scope of the invention. For example, in some embodiments, a catheter may include a tissue collection chamber disposed proximally of the tissue-removing element in use. In such embodiments, the tissue-removing element can comprise a tissue-receiving passage extending axially through the distal end of the tissue-removing element radially inward of the depth stop to direct removed tissue through the tissue-receiving passage and into the proximal tissue collection chamber.

In one example, the catheter 2 including the tissue-removing element 104, 104' may be used to treat in-stent restenosis. An exemplary method of using the tissue-removing element 104 in an in-stent restenosis removal procedure will now be briefly discussed. Although an in-stent restenosis removal procedure is specifically discussed, it will be understood that the tissue-removing element 104 may be used in other tissue-removing applications without departing from the scope of the invention. As is generally known in the art, in an in-stent restenosis removal procedure, tissue is removed from a blood vessel in which a stent was placed in a prior procedure. As explained in more detail below, the catheter including the tissue-removing element 104, 104' may be particularly suitable for use in treating in-stent restenosis because it is believed that the tissue-removing element self-disengages from the stent before becoming entangled and/or restricts a maximum cutting depth to prevent cutting through a stent strut.

In a suitable in-stent restenosis removal procedure, a user inserts the catheter 2 into the blood vessel (such as by using a guidewire), positions the tissue-removing element 104, 104' in the deployed position near the mouth of the stent, and rotates the tissue-removing element in the cutting direction R as the catheter advances axially through the blood vessel and the interior of the stent. The cutting edge 118 engages soft tissue in the interior of the stent as the tissue-removing element 104 rotates. The rotation of the cutting edge 118 cuts through the soft tissue or scrapes the soft tissue away from the inner wall of the stent as the tissue-removing element advances axially. The advancement of the tissue-removing element 104 directs cut tissue inward toward the tissue-receiving depression 140. Cut soft tissue flexes to travel over the depth stop 130 as the tissue-removing element 104 advances. The soft tissue travels radially inward and is received in the tissue-receiving depression, which redirects the tissue toward the tissue collection chamber 112.

If the cutting edge 118 engages a hard object, such as the stent (e.g., a stent strut), the cutting edge may form a shallow cut in the hard object. But before the cutting edge 118 cuts deeper into the hard object, it is believed that the engagement surface 132 of the depth stop 130 will engage the hard object to limit the depth of the cut. The hard material does not flex like the soft tissue, so the engagement between the depth stop 130 and the hard object stalls further advancement of the catheter 2 into the hard object. In one embodiment, the depth stop 130 is shaped and arranged relative to the cutting edge 118 to restrict the tissue-removing element 104 to a maximum cutting depth that is less than the thickness of the stent struts of the stent from which tissue is removed during the in-stent restenosis removal procedure. In certain embodiments, the engagement between the hard object and the depth stop 130 imparts reactionary forces on the tissue-removing element 104 that causes the cutting edge 118 to back out of the cut formed in the hard object. In this sense, it is believed the tissue-removing element 104 is, in certain embodiments, configured to self-disengage with a stent strut to prevent entanglement with the stent.

As can be seen, it is believed the tissue-removing element 104 can be used to remove soft tissue from a body lumen without damaging hard objects therein. It is believed the depth stop 130 limits the cutting depth of the tissue-removing element 104 in hard objects. It is further believed that the cutting element 104 can be used, for example, to remove soft tissue from a stent in a blood vessel without cutting through the struts that form the stent. Moreover, in some embodiments, it is believed engagement between the depth stop 130 and a hard stent strut causes the catheter 2 to back out of a cut formed in the strut, which prevents entanglement with the stent.

Where dimensional ranges are cited in the present disclosure, it should be understood that the range is inclusive of the end points of the range, unless otherwise indicated. For example, a range of "between about 1 inch and about 2 inches" includes lengths of about 1 inch and about 2 inches and all of the lengths between those two end points of the range.

When introducing elements of the present invention or the one or more embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatuses, systems, and methods without departing from the scope of the invention, it is intended that all matter contained in the above description and shown in the accompanying drawings shall be interpreted as illustrative and not in a limiting sense.

What is claimed is:

1. A tissue-removing element configured for a tissue-removing catheter, the tissue-removing element comprising:
    a tissue-removing element body having opposite first and second axial ends and an axis extending through the first and second axial ends;
    an annular cutting edge at the first axial end of the tissue-removing element body extending around the axis of the tissue-removing element body;
    an annular depth stop at the first axial end of the tissue-removing element body extending around the axis of the tissue-removing element body and being disposed radially inward of the cutting edge relative to the axis of the tissue-removing element body, the annular depth stop having an engagement surface at an axial end thereof configured to restrict a cutting depth of the annular cutting edge, wherein the annular cutting edge and the annular depth stop intersect one another at an annular junction, wherein the annular cutting edge and the annular depth stop extend directly from the annular junction in the same axial direction, wherein the annular depth stop has a uniform cross-sectional shape around the axis of the tissue-removing element body; and
    a concave tissue-receiving depression defined by the first axial end of the tissue-removing element body, wherein the tissue-receiving depression is radially inward of the annular depth stop and the tissue-receiving depression is radially inward of the annular junction, and wherein the tissue-receiving depression is configured to direct removed tissue in the axial direction.

2. A tissue-removing element as set forth in claim 1, wherein the engagement surface has a generally convex cross-sectional shape.

3. A tissue-removing element as set forth in claim 1, wherein the cutting edge protrudes axially beyond the annular depth stop.

4. A tissue-removing element as set forth in claim 3, wherein the cutting edge is axially spaced apart from the axial end of the annular depth stop a distance of from about 0.0005 inches (0.0127 mm) to about 0.010 inches (0.254 mm).

5. A tissue-removing element as set forth in claim 1, wherein the annular depth stop protrudes axially beyond the cutting edge.

6. A tissue-removing element as set forth in claim 5, wherein the axial end of the annular depth stop is axially spaced apart from the cutting edge a distance from about 0.0005 inches (0.0127 mm) to about 0.010 inches (0.254 mm).

7. A tissue-removing element as set forth in claim 1, wherein the cutting edge and the axial end of the annular depth stop are located at about the same axial position.

8. A tissue-removing element as set forth in claim 1, wherein the axial end of the annular depth stop is radially spaced apart from the cutting edge a distance from about 0.001 inches (0.0254 mm) to about 0.02 inches (0.508 mm).

9. A tissue-removing element as set forth in claim 1, wherein the annular cutting edge is defined by a radially outer blade surface and a beveled radially inner blade surface intersecting one another.

10. A tissue-removing element as set forth in claim 9, wherein the inner blade surface and the engagement surface define an annular gap therebetween.

11. A tissue-removing element as set forth in claim 9, wherein the radially inner blade surface intersects the engagement surface at the annular juncture.

12. A tissue-removing element as set forth in claim 11, wherein the inner blade surface and the engagement surface extend away from the annular juncture in radially opposite directions.

13. A tissue-removing element as set forth in claim 1, further comprising a tissue-receiving depression formed in the first axial end of the tissue-removing element body radially inward of the annular depth stop.

14. A tissue-removing element as set forth in claim 1, further comprising a tissue-receiving passage extending axially through the first axial end of the tissue-removing element body radially inward of the depth stop.

15. A tissue-removing element as set forth in claim 1, in combination with a catheter including a driveshaft operatively connected to the tissue-removing element and configured to rotate the tissue-removing element about the axis of the tissue-removing element body.

16. A tissue-removing catheter for removing tissue from a body lumen, the tissue-removing catheter comprising:
    a rotatable driveshaft; and
    a tissue-removing element coupled to the rotatable driveshaft for rotating the tissue-removing element about an axis of rotation, the tissue-removing element having opposite first and second axial ends spaced apart along the axis of rotation, the tissue-removing element comprising:
    an annular cutting edge at the first axial end of the tissue-removing element extending around the axis of rotation of the tissue-removing element;
    an annular depth stop at the first axial end extending around the axis of rotation of the tissue-removing element and being disposed radially inward of the cutting edge relative to the axis of rotation of the tissue-removing element, the annular depth stop having an engagement surface at an axial end thereof configured to restrict a cutting depth of the annular cutting edge, wherein the annular cutting edge and the annular depth stop intersect one another at an annular junction, wherein the annular cutting edge and the annular depth stop extend directly from the annular junction in the same axial direction, wherein the annular depth stop has a uniform cross-sectional shape around the axis of the tissue-removing element body; and
    a concave tissue-receiving depression defined by the first axial end of the tissue-removing element body, wherein the tissue-receiving depression is radially inward of the annular depth stop and the tissue-receiving depression is radially inward of the annular junction, wherein the tissue-receiving depression is configured to direct removed tissue in the axial direction.

17. A tissue-removing catheter as set forth in claim 16, wherein the engagement surface has a generally convex cross-sectional shape.

18. A tissue-removing element as set forth in claim 16, wherein the cutting edge protrudes axially beyond the annular depth stop.

\* \* \* \* \*